US009801788B2

(12) United States Patent
Banik et al.

(10) Patent No.: US 9,801,788 B2
(45) Date of Patent: Oct. 31, 2017

(54) DRUG VIAL SAFETY DEVICE

(71) Applicant: Becton, Dickinson and Company, Franklin Lakes, NJ (US)

(72) Inventors: Robert Banik, Edgewater, NJ (US); Edward Rosen, Morristown, NJ (US); John Manocchio, River Edge, NJ (US); James Bates, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 425 days.

(21) Appl. No.: 14/391,362

(22) PCT Filed: Apr. 8, 2013

(86) PCT No.: PCT/US2013/035655
§ 371 (c)(1),
(2) Date: Oct. 8, 2014

(87) PCT Pub. No.: WO2013/155055
PCT Pub. Date: Oct. 17, 2013

(65) Prior Publication Data

US 2015/0105745 A1 Apr. 16, 2015

Related U.S. Application Data

(60) Provisional application No. 61/686,608, filed on Apr. 9, 2012.

(51) Int. Cl.

| | |
|---|---|
| ***A61B 19/00*** | (2006.01) |
| ***A61J 1/20*** | (2006.01) |
| ***A61J 1/14*** | (2006.01) |

(52) U.S. Cl.
CPC .......... *A61J 1/2096* (2013.01); *A61J 1/1412* (2013.01); *A61J 1/1406* (2013.01); *A61J 1/1481* (2015.05); *A61J 1/202* (2015.05); *A61J 1/2065* (2015.05); *A61J 2205/40* (2013.01)

(58) Field of Classification Search
CPC ...... A61J 1/2096; A61J 1/1412; A61J 1/1481; A61J 1/202; A61J 1/2065; A61J 1/1406
USPC .............................................. 604/403–416
See application file for complete search history.

(56) References Cited

U.S. PATENT DOCUMENTS

| | | | | |
|---|---|---|---|---|
| 4,211,439 | A | 7/1980 | Moldestad | |
| 4,442,946 | A | 4/1984 | MacDonald et al. | |
| 4,619,640 | A | 10/1986 | Potolsky et al. | |
| 4,671,331 | A * | 6/1987 | Pruden | A61J 1/20 141/125 |
| 5,125,921 | A * | 6/1992 | Duschek | B65D 51/002 215/247 |
| 5,230,429 | A | 7/1993 | Etheredge | |

(Continued)

FOREIGN PATENT DOCUMENTS

| | | | |
|---|---|---|---|
| DE | 20109061 | U1 | 8/2001 |
| EP | 0769456 | A2 | 4/1997 |
| WO | WO-2012/020083 | A1 | 2/2012 |

*Primary Examiner* — Philip R Wiest
(74) *Attorney, Agent, or Firm* — Dickinson Wright PLLC

(57) ABSTRACT

A drug vial safety device, including a cover that is securable to a drug vial is disclosed. The cover at least partially encloses at least a neck and a lid of the drug vial. The cover includes a port having a shape that restricts syringe access to the vial through the port to a syringe shaped to be compatible with the port shape.

39 Claims, 15 Drawing Sheets

(56) References Cited

U.S. PATENT DOCUMENTS

| | | | | |
|---|---|---|---|---|
| 5,405,031 | A * | 4/1995 | Derksen | B65D 51/002 215/237 |
| 5,423,791 | A * | 6/1995 | Bartlett | A61J 1/2096 604/403 |
| 5,725,511 | A | 3/1998 | Urrutia | |
| 5,776,124 | A | 7/1998 | Wald | |
| 5,851,035 | A | 12/1998 | Marc et al. | |
| 5,931,826 | A | 8/1999 | Faulks et al. | |
| 5,931,828 | A * | 8/1999 | Durkee | B65D 47/08 215/247 |
| 6,190,364 | B1 | 2/2001 | Imbert | |
| 6,293,595 | B1 | 9/2001 | Marc et al. | |
| 6,402,207 | B1 | 6/2002 | Segal et al. | |
| 6,508,807 | B1 | 1/2003 | Peters | |
| 6,571,837 | B2 | 6/2003 | Jansen et al. | |
| 6,612,624 | B1 | 9/2003 | Segal et al. | |
| 7,137,654 | B2 | 11/2006 | Segal et al. | |
| 8,091,727 | B2 | 1/2012 | Domkowski | |
| 8,684,979 | B2 | 4/2014 | Deighan et al. | |
| 2001/0003996 | A1 * | 6/2001 | Jansen | A61J 1/1406 141/329 |
| 2007/0060898 | A1 | 3/2007 | Shaughnessy et al. | |
| 2009/0099552 | A1 | 4/2009 | Levy et al. | |
| 2009/0120934 | A1 * | 5/2009 | Domkowski | A61J 1/1406 220/253 |
| 2010/0283238 | A1 | 11/2010 | Deighan et al. | |
| 2011/0144614 | A1 | 6/2011 | Hereford | |
| 2011/0144626 | A1 | 6/2011 | Hall | |
| 2012/0059346 | A1 | 3/2012 | Sheppard et al. | |

* cited by examiner

DRUG VIAL SAFETY DEVICE

CROSS-REFERENCE TO RELATED APPLICATIONS

This application claims priority under 35 USC §119(e) from U.S. Provisional Patent Application Ser. No. 61/686,608 filed on Apr. 9, 2012, the disclosure of which is incorporated herein by reference in its entirety.

FIELD OF THE INVENTION

The present invention relates to a drug vial safety device. More particularly, the present invention relates to a safety device that is attached to a drug vial to restrict access to geometrically mismatched syringes while facilitating user removal of a vial cap.

BACKGROUND OF THE INVENTION

Currently, there is a desire for safeguards in the medical industry to prevent the delivery of erroneous medications and doses to patients. Unfortunately, errors in the administration of medications can result in patient injury or fatality, and are often the result of preventable human error. Even though a patient may fully recover from the delivery of an erroneous medication, the injuries sustained and the recuperation could have staggering patient costs due to prolonged hospital stays.

One factor in the inadvertent delivery of erroneous medication is the interchangeability and compatibility of standard universal medical connectors and infusion/injection devices. Many medical connectors and infusion/injection devices are universal couplers that are designed to mate with and accept most syringes and fluid delivering devices.

Because of this interchangeability, errors can be made in interconnecting needleless syringes, catheters, infusion bags, infusion pumps, tubing, intravenous ports, vials, and other drug delivery components. For example, misconnection errors can involve enteral feeding tubes and intravenous catheters. Enteral feeding tubes are used to administer liquid nutritional solutions and medications directly to a patient's gastrointestinal system. In contrast, intravenous catheters are used to administer medications and the like directly to a patient's vascular system. Patients may be harmed if feeding solutions are administered intravenously and vice versa.

Moreover, contemporary medical vials generally provide unobstructed access to any syringe for the withdrawal of medicament. Often, drugs or medicament are available in multiple concentrations in medical vials. Medical delivery problems can arise when a syringe with scale markings designed for a higher concentration of a particular drug is inadvertently used to withdraw a lower concentration version of the drug from the vial, or vice versa, leading to the dangerous prospect of administrating an improper dosage to the patient.

The contemporary medical equipment also lacks a device that helps facilitate the withdrawal of medication from a vial. Typically, vials are manufactured with sealing caps that have to be manually pried off the vials by a health care provider or user prior to use. Some individuals may lack the manual dexterity required to pry off the sealing cap and therefore, may encounter great difficulty in opening such sealing caps.

Additionally, to accommodate such limited-dexterity users, manufacturers typically have to manufacture longer syringe needles to allow these individuals to reliably gain access to the medicine contained within the vial. For example, the longer syringe needles can be required if the syringe needle penetrates the vial septum off-center, or if the syringe needle penetrates the vial septum in a direction that is not substantially perpendicular to the vial septum.

Accordingly, there is a need for a safety device that safeguards against improper fluid path connections between medical components, particularly between a syringe and a drug or other medicament vial. Also, there is a need for a device to help a health care provider or other user withdraw medication from a vial.

Similarly, there exists a need for a drug vial safety device that restricts unintended and improper syringe access to a drug or medicament vial.

There also exists a need for fixedly attaching a drug vial safety device to the neck of a vial during packaging of the vial, to prevent drug delivery errors.

Finally, there exists a need for the fixedly attached drug vial safety device to help facilitate user removal of a vial cap and ensure proper positioning of a syringe needle to reliably gain access to the medicament contained within the vial.

SUMMARY OF EMBODIMENTS OF THE INVENTION

An aspect of the present invention is to substantially address the above and other concerns, and provide a drug vial safety device that restricts unintended and improper syringe access to a drug or other medicament vial.

Another aspect of the present invention is to provide a drug vial safety device that is fixedly attached to a neck of a vial during packaging of the vial, to prevent end user drug delivery errors.

Another aspect of the present invention is to provide a fixedly-attached drug vial safety device that helps facilitate user removal of a vial cap and ensure proper positioning of a hollow syringe needle to reliably gain access to the medicament contained within the vial.

The foregoing and/or other aspects of the present invention are achieved by providing a drug delivery device, including a cover securable to drug vial to at least partially enclose at least a neck and a lid of the drug vial. The cover includes a port having a shape that restricts syringe access to the vial through the port to a syringe shaped to be compatible with the port shape.

The foregoing and/or other aspects of the present invention are also achieved by providing a method of ensuring proper correlation between medicament in a drug vial and a syringe. The method includes providing a syringe with a shaped portion and a hollow needle, and securing a cover to the drug vial to at least partially enclose at least a neck and a lid of the drug vial. The cover includes a port having a shape that is compatible with the shaped syringe portion. The port permits passage of at least part of the shaped syringe portion therethrough to provide the needle with access to the medicament within the drug vial.

The foregoing and/or other aspects of the present invention are also achieved by providing a drug vial safety device, including a cover securable to drug vial to at least partially enclose at least a neck and a lid of the drug vial. The cover includes a port having a shape that permits at least a portion of a compatibly-shaped syringe to pass therethrough, to limit access to medicament within the drug vial.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
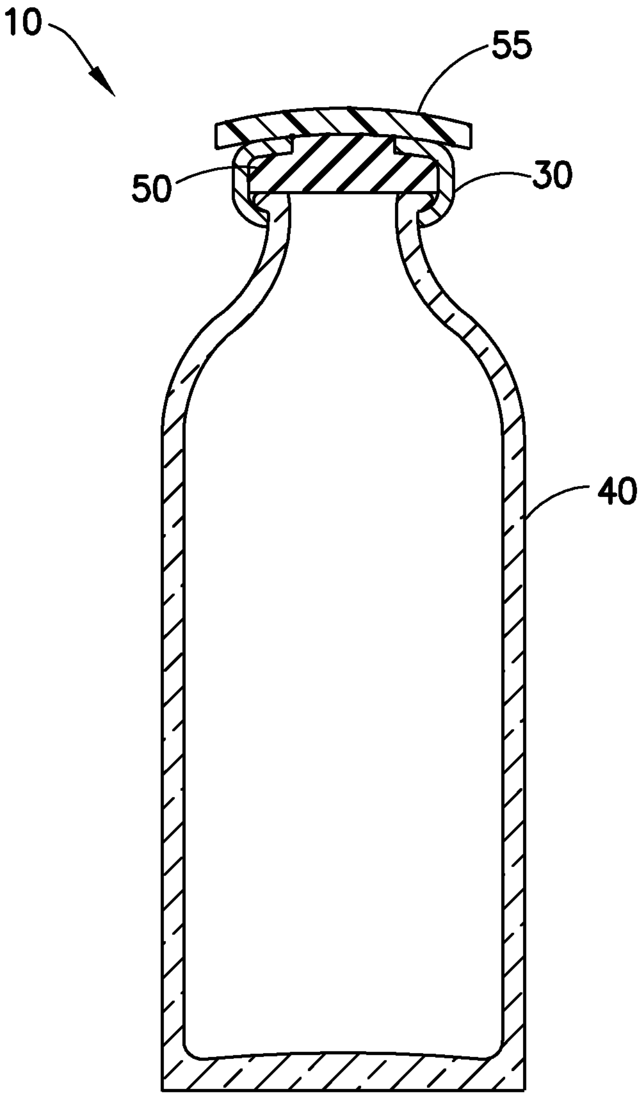
FIG. 1 is a cross-sectional view of a conventional drug or other medicament vial.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

FIG. 1 is a cross-sectional view of a conventional vial 10 for containing a drug or other medicament. For brevity, the term “drug” will be used hereinafter in place of phrase “drug or other medicament.” The vial 10 includes a vial body 40 that is generally made of glass or plastic, a septum 50, and a lid 30 securing the septum 50 to the vial body 40 and together therewith, forming an access or inlet port to the vial body 40. The drug vial 10 also includes a protective and sanitary cap 55 to prevent damage and contamination of the septum 50 prior to use.

In general, embodiments of the inventive vial safety device are fixedly attached to the neck of a vial to restrict access to unintended syringes with improper scale markings, that is, syringes with scale markings that do not correspond to the concentration of the drug in the vial. It will be understood, however, that the cover can envelop all or substantially all of the vial without departing form the present invention’s scope. Embodiments of the inventive vial safety device shroud the inlet port of a vial and only permit access to the inlet port by specific geometrically-matched or geometrically compatible syringes. For example, according to one embodiment, the vial safety device provides a geometrically-shaped female port for receiving a geometrically matching male portion of a syringe hub or flange.

Preferably, no modifications are required to incorporate the vial safety device to existing vials. The vial safety device is simply fixedly snapped onto the existing vial prior to packaging the vial. In such a case, because the existing vial is supplied and delivered with the vial safety device shrouding the inlet ports of the vials, embodiments of the inventive vial safety device provide various ways to facilitate user removal of the vial sealing caps.

Figure 4:
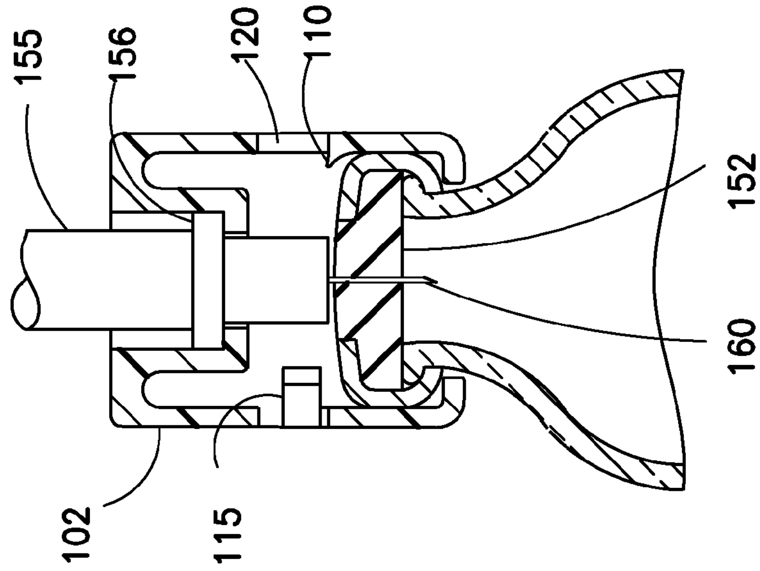
FIGS. 3 and 4 are cross-sectional views illustrating operation of the safety device of FIG. 2.
Figure 2:
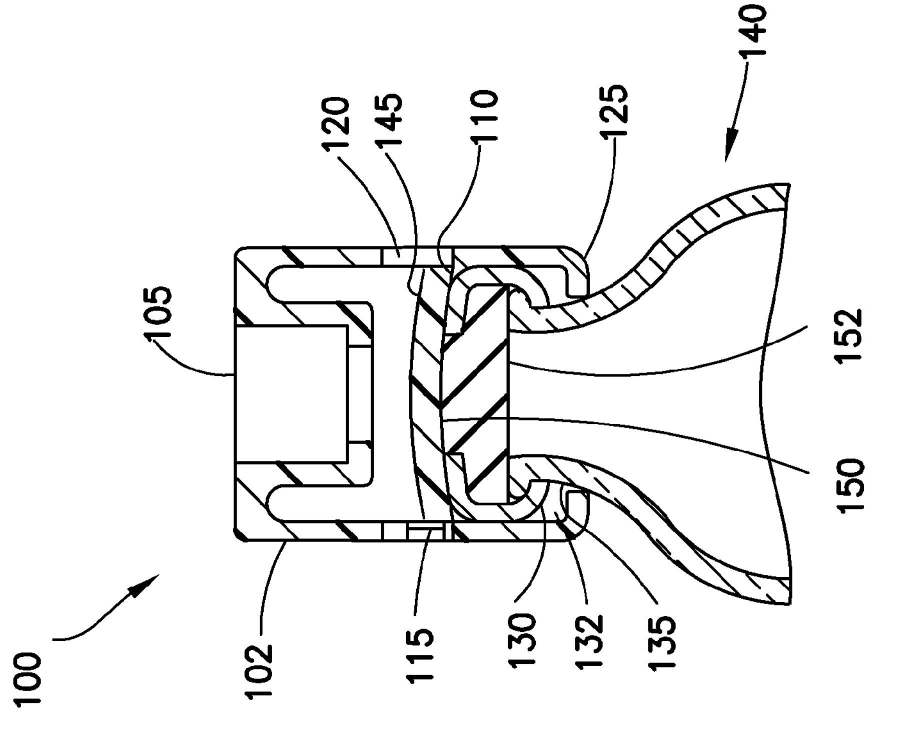
FIG. 2 is a cross-sectional view of a drug vial safety device in accordance with a first embodiment of the present invention.
Figure 3:
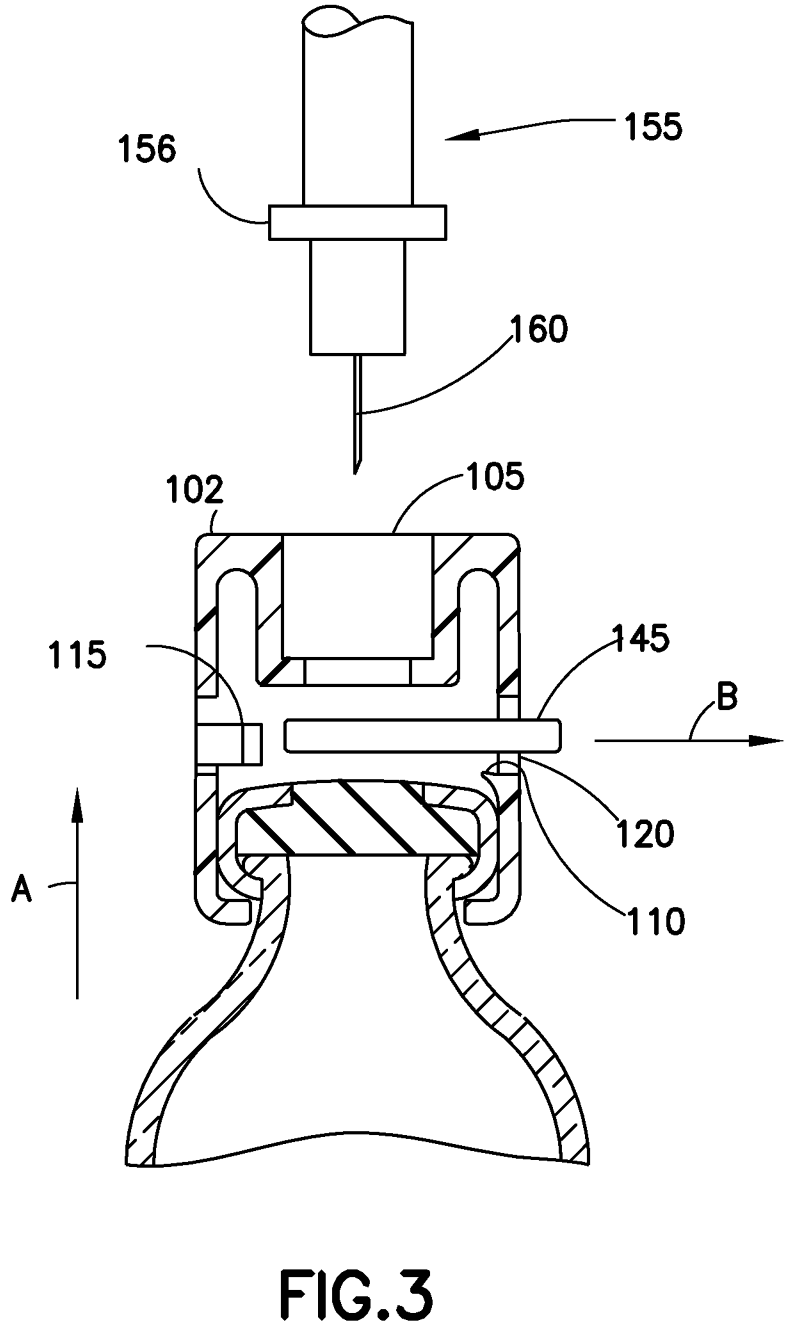

Referring to FIGS. 2-4, a first embodiment of a vial safety device 100 with a side cantilever cap removal feature is illustrated. The vial safety device 100 includes a cover 102, a geometrically-shaped female port 105, a first cantilever 110, a second cantilever 115, an ejection window 120, and a bottom lip 125.

According to one embodiment, the bottom lip 125 of the vial safety device 100 is snap-fit over a lid 130 and onto a neck portion 135 of a vial 140 by the manufacturer prior to packaging. Prior to user activation of the vial safety device 100, the first cantilever 110 and the second cantilever 115 are collapsed against the vial lid 130 and a space 132 is maintained between the bottom lip 125 of the vial safety device 100 and the vial lid 130. Although a user other than medicament recipient (for example, a health care professional) can use the vial safety device 100, for brevity the term “user” will be employed hereinafter to refer to a patient and/or other user.

The user activates the vial safety device 100 by pulling the vial safety device 100 in a distal direction away from the vial 140. The vial safety device 100 moves distally in until the bottom lip 125 abuts the vial lid 130, as shown in FIG. 3. As the vial safety device 100 is moved distally away from the vial 140, the first cantilever 110 functions as a cap-separating portion of the device 100 and breaks the vial cap 145 from a vial inlet port 150, to expose a portion of the septum or bung 152. Additionally, the second, inwardly biased cantilever 115, which is freed by the distal motion of the vial safety device 100, extends to eject the vial cap 145 out of the window 120 of the vial safety device 100. According to one embodiment, the second cantilever or cantilevered arm 115 is initially disposed against the side of the lid 130. According to an alternative embodiment, the second cantilever 115 is initially disposed against the side of the cap 145. Although depicted as being a circumferential cantilevered arm 115, the arm 115 can also be axially cantilevered, or can extend at an angle to both the longitudinal axis and the circumference of the vial safety device 100.

Additionally, although the first cantilever 110 is depicted as being fixed in FIGS. 2-4, according to an alternative embodiment, the first cantilever 110 can be an inwardly biased cantilevered arm 110 that is initially disposed against the side of the lid 130, and that is freed by distal movement of the vial safety device 100 to extend radially inward to engage a proximal side of the cap 145, and subsequently break the cap 145 free from the port 150 upon further distal movement of the vial safety device 100.

As shown in FIGS. 3 and 4, subsequent to activation, the vial safety device 100 is ready to permit a syringe 115 with a geometrically matching feature 156 to access the drug filled vial 140 by way of the geometrically matching female port 105 of the vial safety device 100. For example, geometric shapes can include, but are not limited to, polygons, triangles, quadrilaterals, circles, trapezoids, pentagons, and other non-symmetrical shapes. When the size and shape of the syringe 155 and vial safety device 100 are complementary, the female port 105 of the vial safety device 100 will guide the syringe 155 proximally towards the vial 140 to ensure proper positioning of a hollow syringe needle 160 in relation to the septum of the vial 140. More specifically, not only do the port 105 and complimentary-shaped syringe 155 center the syringe for penetration of the septum 152, they also ensure that the syringe 155 penetrates the septum 152 substantially perpendicularly.

Figure 5:
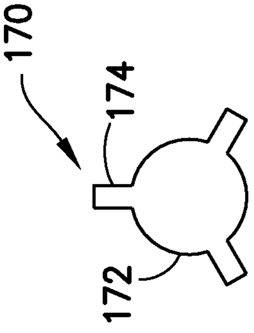
FIGS. 5-14 illustrate embodiments of shapes for a port of the safety device of FIG. 2 and/or a corresponding syringe.
Figure 6:
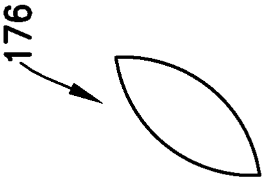
Figure 7:
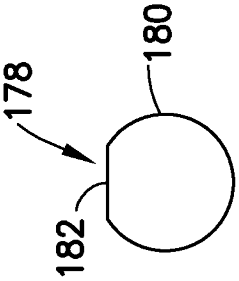
Figure 8:
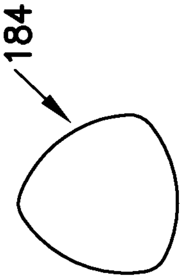
Figure 9:
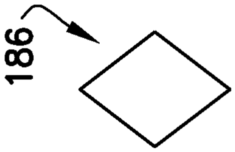
Figure 10:
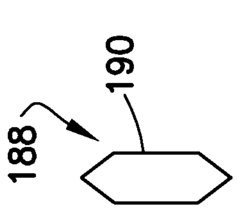
Figure 11:
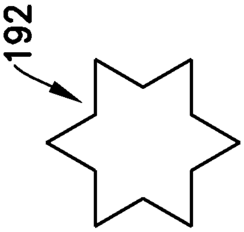
Figure 12:
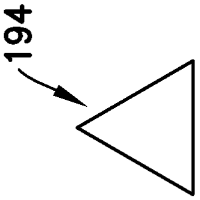
Figure 13:
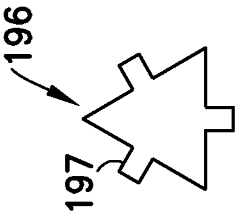
Figure 14:
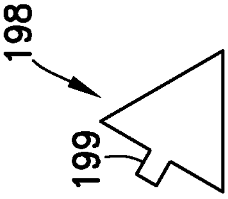
Figure 15:
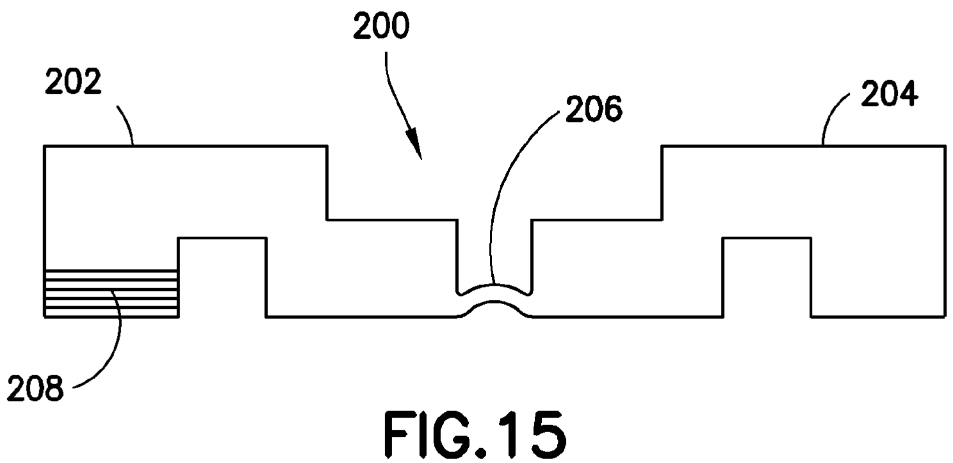
FIGS. 15-18 illustrate a drug vial safety device in accordance with a second embodiment of the present invention.
Figure 16:
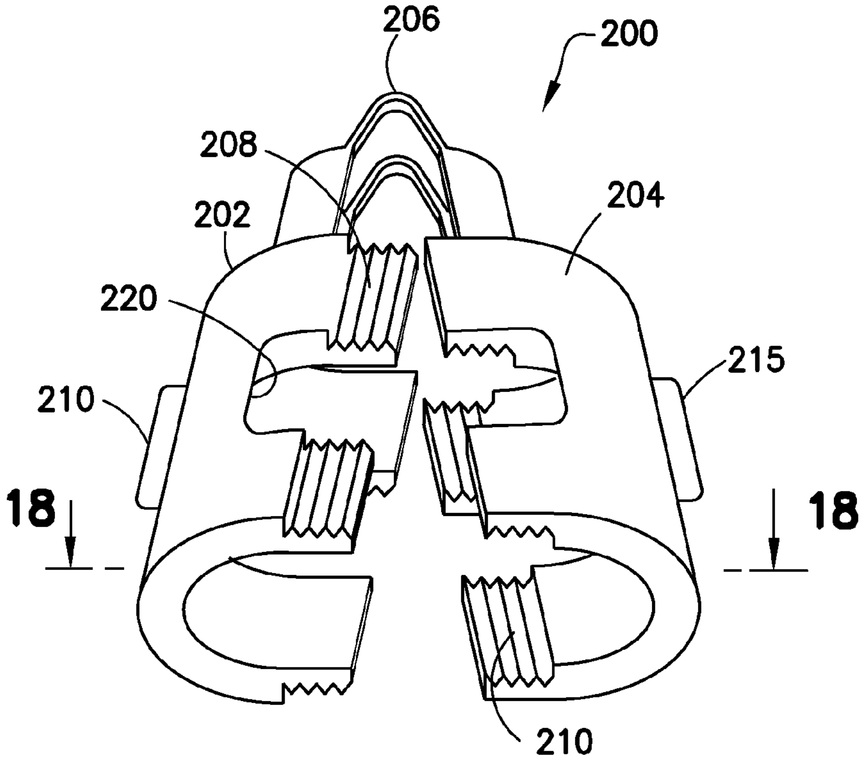
Figure 17:
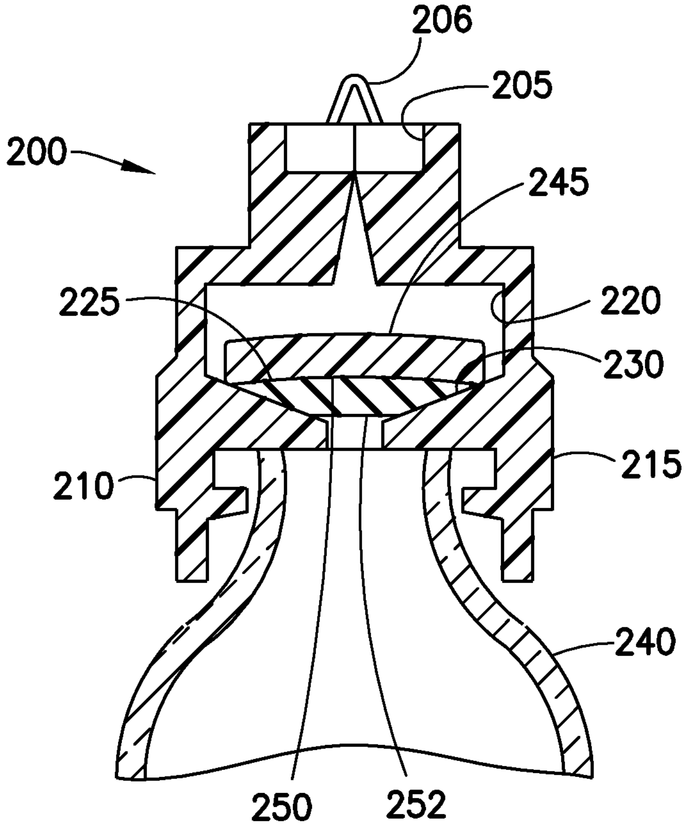
Figure 18:
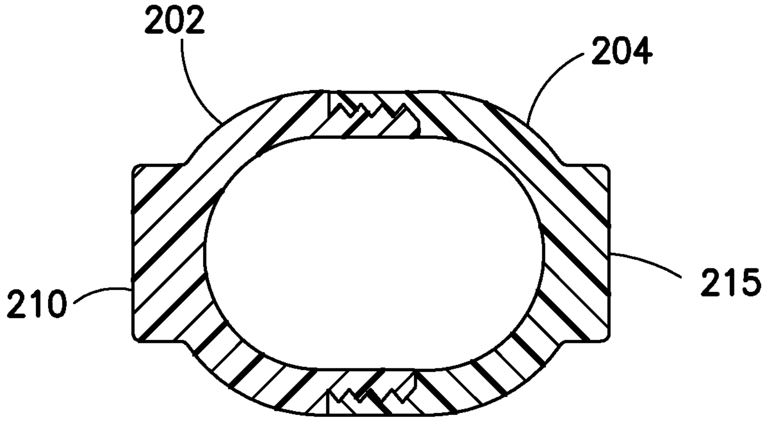
Figure 19:
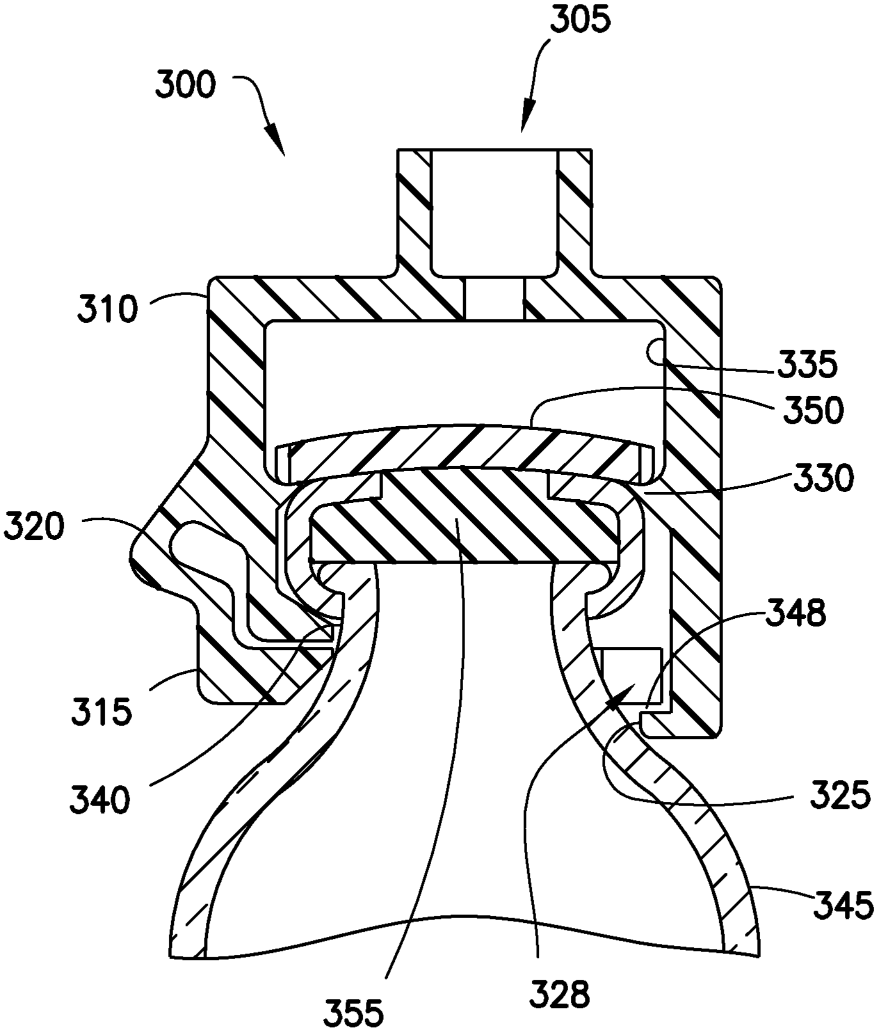
FIGS. 19-22 illustrate a drug vial safety device in accordance with a third embodiment of the present invention.

FIGS. 5-14 illustrate embodiments of shapes for a port of the safety device of FIG. 2 and/or the corresponding syringe 155. For example, as shown in FIG. 5, the port 170 has a circular portion 172 and three wing portions 174 extending from the circular portion 172. Although the wing portions 174 are depicted as being equidistantly spaced about the circular portion 172, it will be understood that other spacing is contemplated without departing from the present invention's scope. FIG. 6 illustrates a football-shaped port 176. In FIG. 7, the port 178 includes a circular portion 180 and a flat portion 182. The port 184 of FIG. 8 has a rounded triangular shape, whereas the port 186 of FIG. 9 has a diamond or rhomboidal shape.

It may be necessary for a port to admit more than one shaped syringe, for example, if drugs need to be mixed prior to injection. Embodiments of the inventive vial safety device can accommodate such needs. For example, although the diamond-shaped port 186 of FIG. 9 would admit a complementary diamond-shaped syringe, a syringe with the hexagonal shape 188 of FIG. 10 (effectively, a diamond shape with truncated flat sides 190) could also be admitted to the diamond-shaped port 186. Similarly, a port with the six-pointed star configuration of FIG. 11 could also admit not only a complimentary star-shaped syringe, but could also admit a syringe with the hexagonal shape 188 of FIG. 10, as well as the triangular shape 194 of FIG. 12. Further, the polygonal triangular port 196 with wings 197 could admit a complimentary-shaped syringe as well as a syringe with the polygonal shape 198 of FIG. 14, which has a single wing 199, or similarly-shaped syringe with two wings 199.

It will be understood that port and syringe shape is not the only contemplated discriminating factor; size can also be used. For example, with a port being recessed from a distal surface of an embodiment of the inventive vial safety device, such as that shown in FIG. 2, although a port and a syringe may have the same shape, the port will only admit a syringe if the syringe is smaller than the port. Thus, both size and shape can be used to permit or proscribe syringe access, and can both be factors for designing a system for access by more than one syringe.

In addition, as subsequently described in greater detail, the port can be a wall extending from the top of the vial safety device, and the compatible syringe can mate within the port, outside the port, or can be a sleeve that mates both internally and externally with the wall. The illustrative geometrical shapes and sizes of the depicted ports and the syringes are merely examples and are not meant to be exhaustive of the various alternative designs and embodiments that are encompassed by the disclosed invention.

Referring to FIGS. 15-18, a second embodiment of a vial safety device 200 with a ramp cap removal feature is illustrated. The vial safety device includes first and second portions 202 and 204 that are connected by a hinge 206. The first and second portions 202 and 204 have interlocking teeth 208 and 210. According to one embodiment, to assemble the vial safety device 200 prior to packaging, the manufacturer rotates the first and second portions 202 and 204 toward each other about the hinge 206 to surround a neck portion 235 of a vial 240. This rotation continues until one or more of the teeth 208 are engaged with one or more of the teeth 210.

Once assembled, this embodiment of the vial safety device 200 comprises a geometrically shaped female port 205, a first side button 210, a second side button 215, a window 220, and first and second ramps 225, 230. The first and second ramps 225, 230 of the vial safety device 200 are molded into an interior housing of the vial safety device 200 and both slope inwardly from the interior housing. Prior to user activation of the vial safety device 200, the first and second ramps 225, 230 rest directly beneath a vial cap 245.

The user activates this embodiment of the vial safety device 200 by squeezing the first and second side buttons 210, 215 located on an exterior housing or cover of the vial safety device 200. This causes the first and second ramps 225, 230 to move radially inwardly, thus increasing the height of a slope angle of the ramps beneath the vial cap 245, as well as engaging more of the teeth 208 with the teeth 210. As the height of the slope angles of the ramps 225, 230 increases, the ramps 225, 230 apply upward pressure to a bottom surface of the vial cap 245 causing the vial cap 245 to break off of a vial inlet port 250. A window 220 on the vial safety device 200 allows the vial cap 245 to fall out on either side of the vial safety device 200. Although not shown, similar to the vial safety device 100, one embodiment of the vial safety device 200 includes a cantilevered arm that automatically ejects the cap 245 after it is freed from the vial inlet port 250 to expose a portion of the septum 252.

Subsequent to activation, the vial safety device 200 is ready to permit a geometrically compatible syringe (not shown) to access the drug filled vial 240 by way of the female port 205 of the vial safety device 200. As previously discussed, when the size and/or shape of the syringe and vial safety device 200 are compatible, the female port 205 guides the syringe proximally toward the vial 240 to ensure proper positioning of a hollow syringe needle (not shown) in relation to the septum 252.

Referring to FIGS. 19-22, a third embodiment of a vial safety device 300 with a tilt cap removal feature is illustrated. This embodiment of the vial safety device 300 comprises a geometrically shaped female port 305 on a top portion 310, a collar portion 315 attached to the top portion by a hinge 320, a first cantilever 325, a second side cantilever 330, and a window 335.

Prior to packaging, the collar portion 315 of the vial safety device 300 is fixedly attached to a neck portion 340 of a vial 345. The top portion 310 of the vial safety device 300, which is attached to the collar portion 315 via a hinge 320, is flipped over the top of a vial inlet port so that the first cantilever 325 is snap-fit beneath a portion of the collar 315 on the side opposite to the hinge 320.

Prior to user activation of the vial safety device 300, a space exists above a lip of the first cantilever 325 and below the collar portion opposite the hinge to allow a clearance to subsequently tilt the safety device 300.

The user activates this embodiment of the vial safety device 300 by tilting the vial device 300 towards the hinge side of the device. The space 348 between the lip of the first cantilever 325 and the collar portion 315 opposite to the hinge allows a clearance for tilting the vial safety device 300. This tilting motion forces the second cantilever 330 upward to pop a vial cap 350 from the vial inlet port and expose a portion of the septum 355. A window 335 on the vial safety device 300 allows the vial cap 350 to fall out on either side of the vial safety device 300. Although not shown, like the previous embodiments, the vial safety device 300 can include an automatic cap-ejecting mechanism, such as a cantilevered arm that ejects the cap 350 through the window subsequent to the cap 350 being freed from the vial inlet port.

Subsequent to activation, the vial safety device 300 is ready to permit a geometrically compatible syringe (not shown) to access the drug filled vial 345 by way of the female port 305 of the vial safety device 300. As previously discussed, when the size and/or shape of the syringe and vial safety device 300 are compatible, the female port 305 guides the syringe proximally toward the vial 345 to ensure proper positioning of the hollow syringe needle (not shown) in relation to the septum 355.

Figure 20:
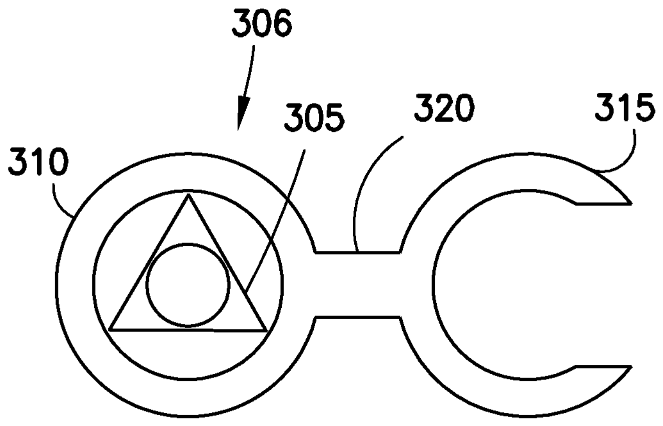
Figure 21:
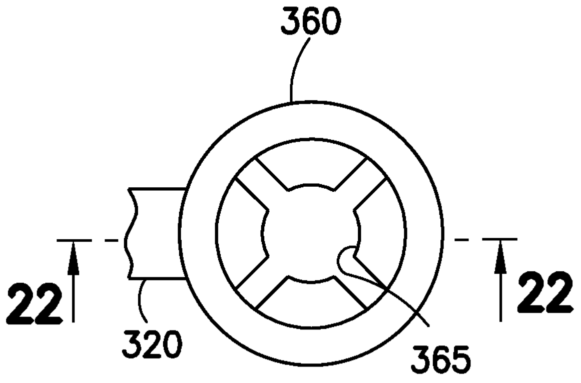
Figure 22:
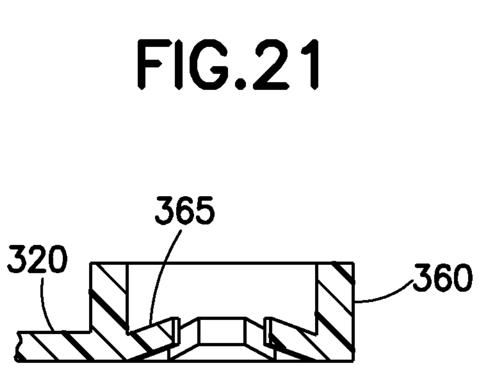
Figure 24:
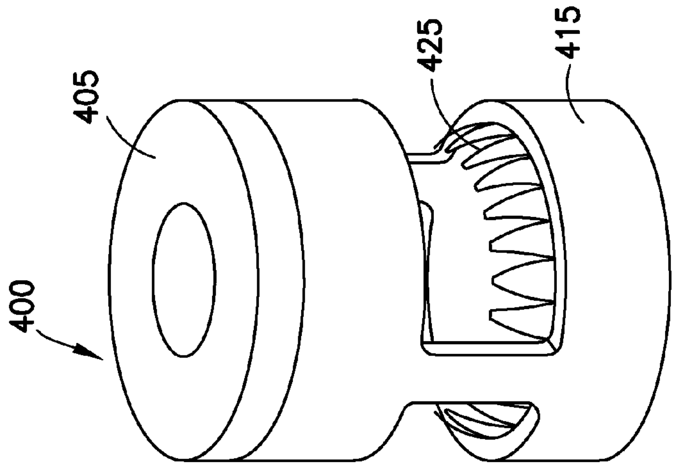
FIGS. 23-28 illustrate a drug vial safety device in accordance with a fourth embodiment of the present invention.

As shown in FIG. 20, the collar portion 315 can be "C-shaped." Alternatively, as shown in FIGS. 21 and 22, the collar portion 360 can be substantially circular and have radially inward protruding teeth 365 that prevent removal of the collar portion 360 from the neck 340 of the vial 345 subsequent to installation. Preferably, as shown in FIG. 22, the teeth are angled distally.

Referring to FIGS. 23-28, a fourth embodiment of a two-piece vial safety device 400 with an axial-motion cantilevered cap removal feature is illustrated. This embodiment of the vial safety device 400 includes a top housing 405 with a geometrically shaped female port 410, a collar portion 415, which is snap-fit to the top housing 405. The collar portion 415 preferably includes two or more cantilevered arms 420, an array of teeth 425, and a window 430. FIGS. 25-28 illustrate an alternative in which the top housing overhangs a portion of the collar portion 415.

Prior to packaging, the collar portion 415 of the vial safety device 400 is fixedly attached to a neck portion 435 of a vial 440, and the top housing 405 of the vial safety device 400 is snap-fit to the collar portion 415 of the vial safety device 400 to shroud an inlet port 445 of the vial 440. Prior to user activation of the vial safety device 400, the two or more cantilevers 420 abut the bottom surface of a vial cap 450. Additionally, a space exists above the array of teeth 425 and below a lid 455 of the vial 440 to allow clearance for a user to activate the device.

Figure 23:
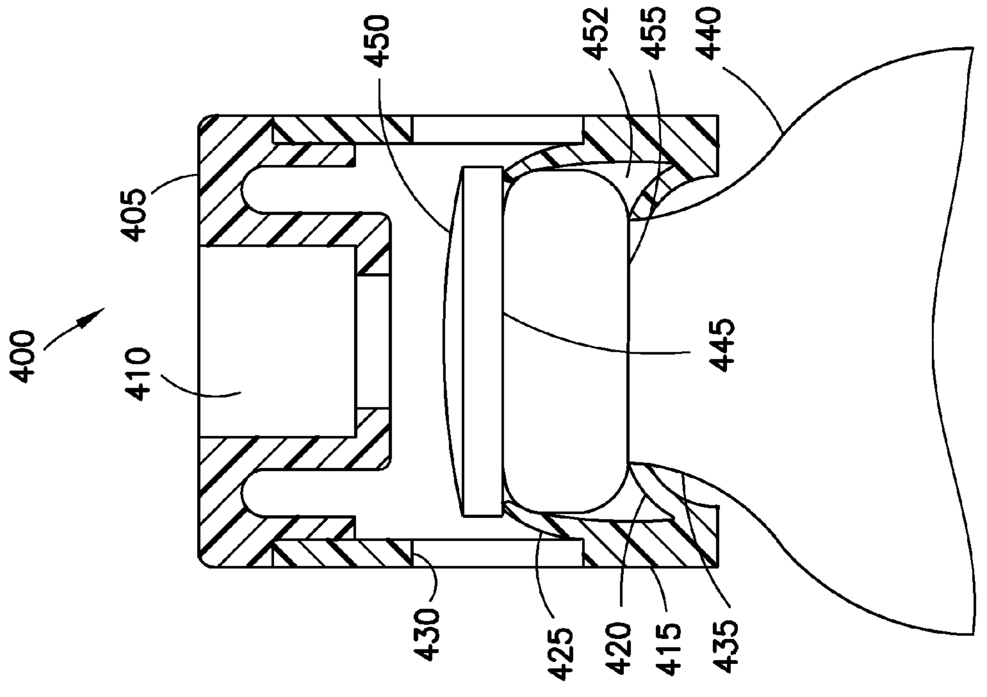
Figure 25:
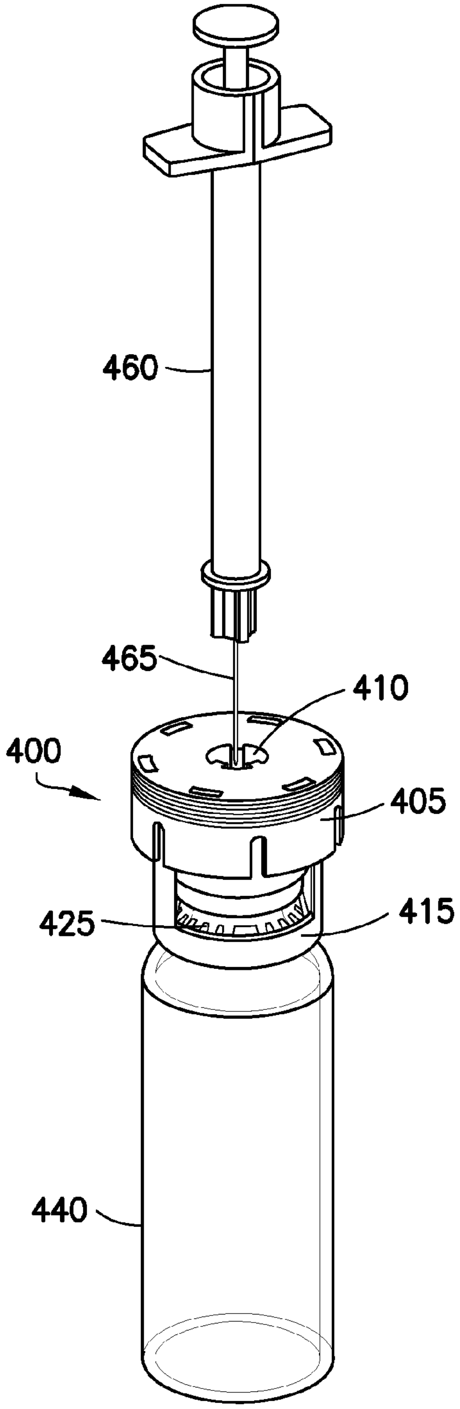
Figure 26:
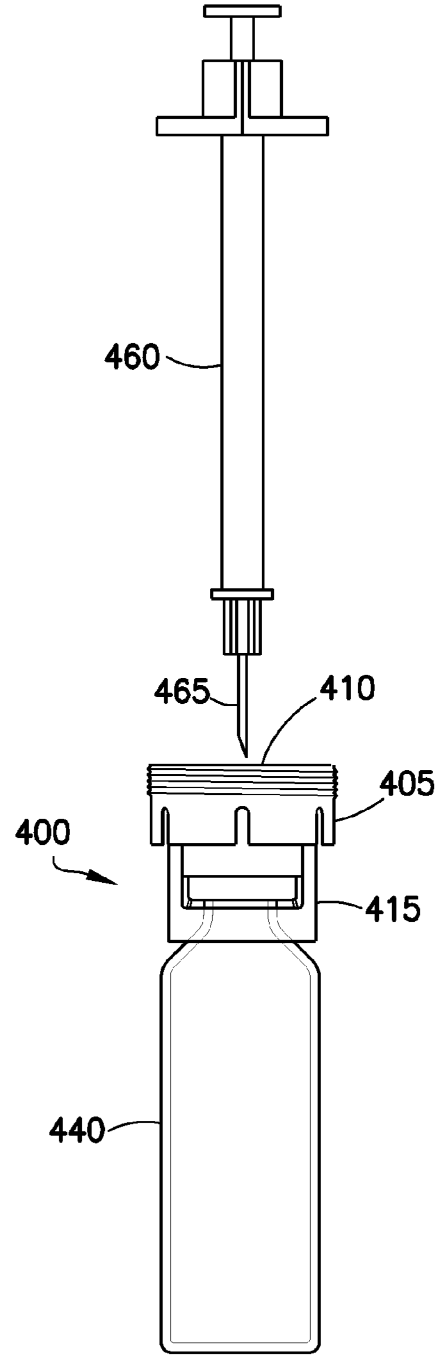
Figure 27:
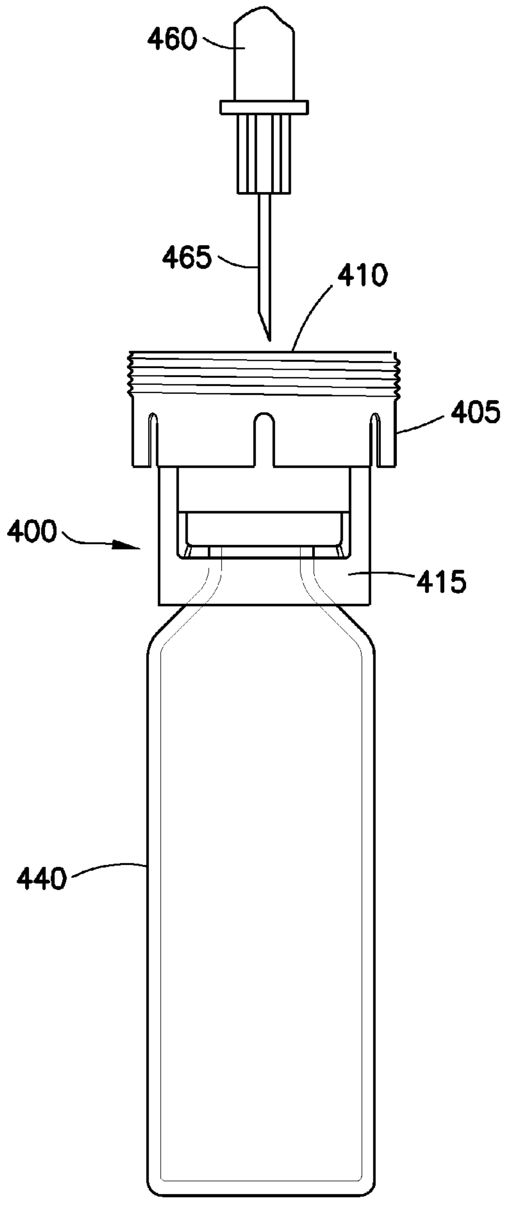
Figure 28:
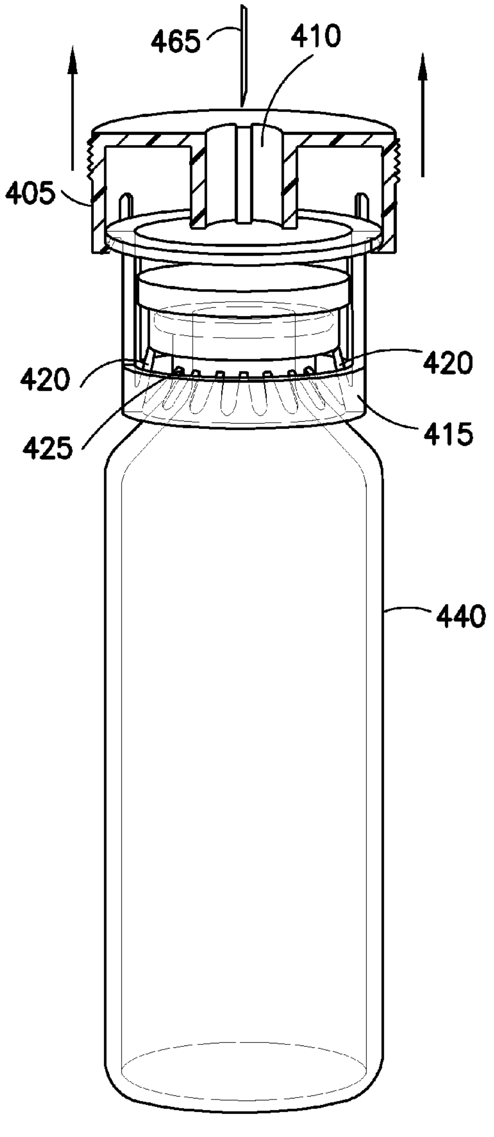
Figure 30:
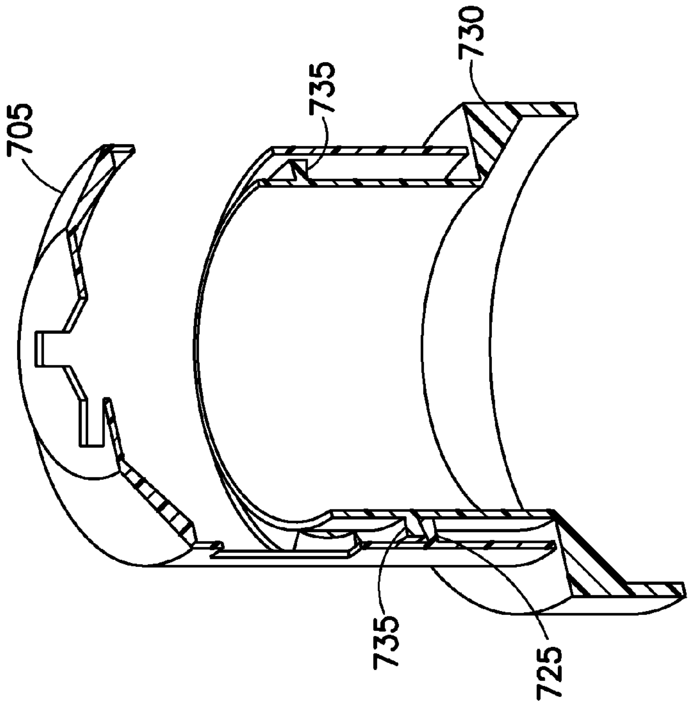
FIGS. 29-33 illustrate a drug vial safety device in accordance with a fifth embodiment of the present invention.
Figure 29:
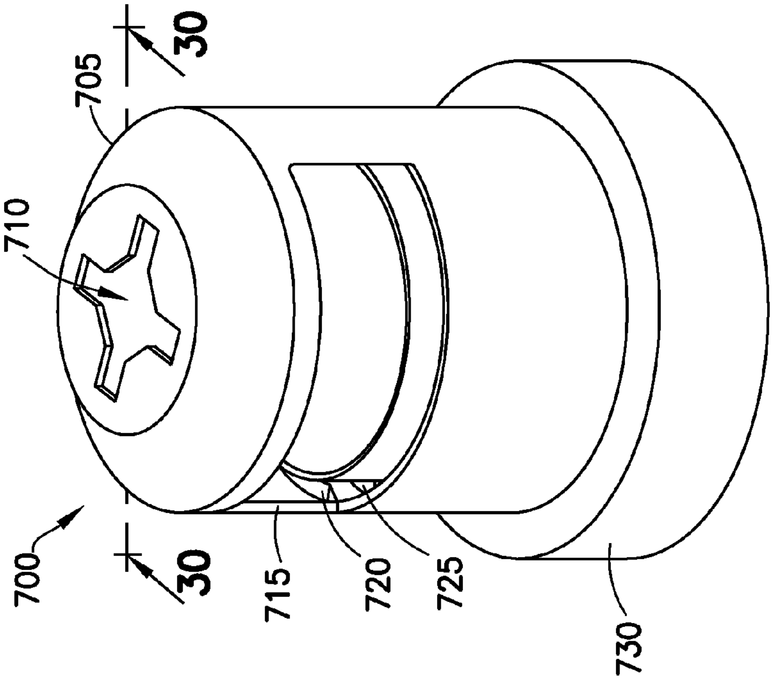
Figure 32:
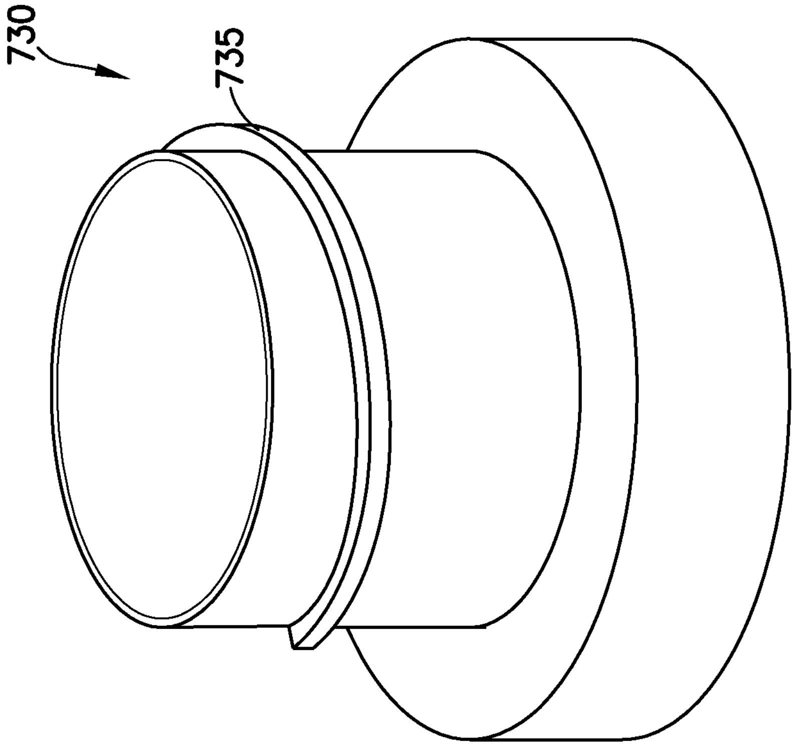
Figure 31:
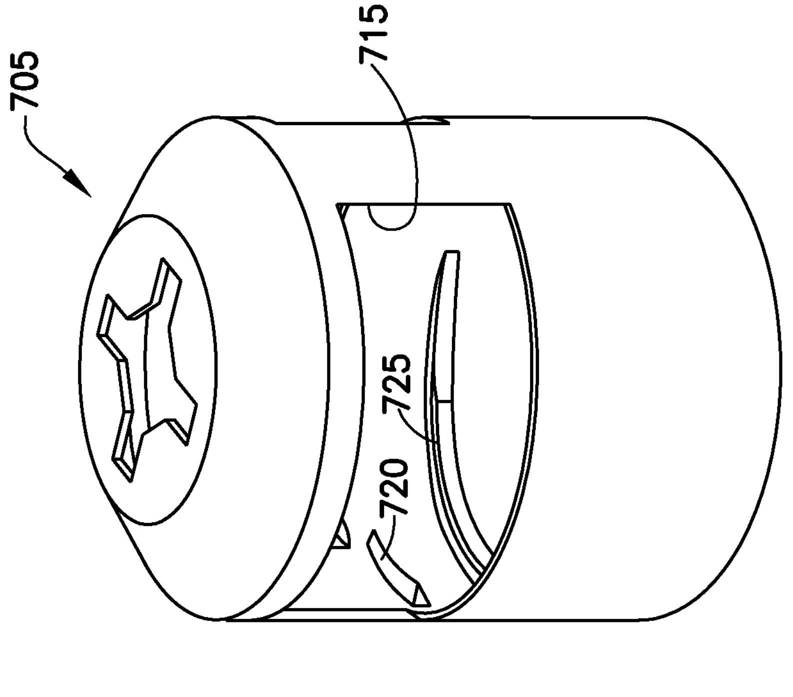

The user activates this embodiment of the vial safety device 400 by pulling the device distally away from the vial 440. FIG. 23 is a partial cross-sectional view of the vial safety device 400 during activation, at a stage immediately prior to the removal of the cap 450. The distal motion causes the teeth 425 to press upwards against the bottom surface of the vial cap 450 to break the vial cap 450 from the vial inlet port 445. The teeth 425 may be the same length to provide parallel removal of the vial cap 450, or they may be unequal in length to cause a tilt and a shearing force, which may provide lower total removal forces.

The window 430 on the vial safety device 400 allows the vial cap 450 to fall out on either side of the vial safety device 400. During activation of the vial safety device 400, the array of teeth 425 lock against the bottom surface of the vial lid 455 to prevent the entire assembly from coming off the vial 440. Although not shown, like the previous embodiments, the vial safety device 400 can include an automatic cap-ejecting mechanism, such as a cantilevered arm that ejects the cap 450 through the window subsequent to the cap 450 being freed from the vial inlet port.

Subsequent to activation, the vial safety device 400 is ready to permit a geometrically compatible syringe (not shown) to access the drug filled vial 440 by way of the female port 410. As previously discussed, when the size and/or shape of the syringe and vial safety device 400 are compatible, the female port 410 guides the syringe proximally toward the vial 440 to ensure proper positioning of a hollow syringe needle 465 in relation to the septum (not shown).

Referring to FIGS. 29-33, a fifth embodiment of a vial safety device 700 with a twist cap removal feature is illustrated. This embodiment of the vial safety device 700 includes an upper member or portion 705 with a geometrically shaped female port 710, a window 715, preferably two or more cantilevers 720, and an upper internal helical thread 725. The vial safety device 700 also includes a bottom member or portion 730 with a lower external helical thread 735 that corresponds to the upper internal helical thread 725. One skilled in the art will appreciate that other mechanisms for connecting the upper and lower portions 705 and 730, for example, a stud and a J-shaped slot, can be employed without departing from the scope of the present invention.

Figure 33:
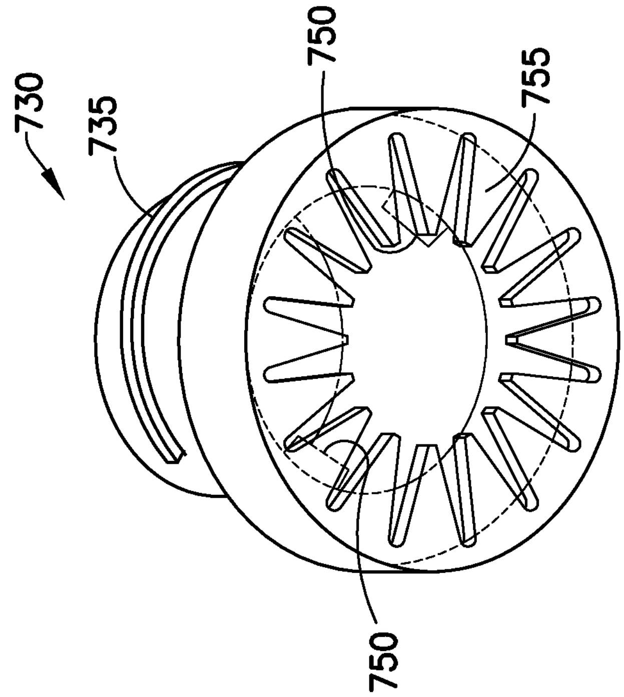

Prior to packaging, the manufacturer fixedly attaches the vial safety device 700 to a vial to shroud an inlet port of the vial. For example, the upper and lower portions 705 and 730 can be threaded together via the threads 725 and 735, and then the vial safety device 700 can be force fit over the distal end of the vial. As shown in FIG. 33, the lower member 730 can include radially inward protruding arms 750 to engage a proximal side of a vial lid to prevent removal of at the vial safety device 700 subsequent to installation. Additionally, the lower member 730 can include a plurality of teeth 755 that substantially prevent rotation of the lower member 730 relative to the vial.

The user activates this embodiment of the vial safety device 700 by twisting the top portion 705 relative to the lower portion 730. According to one embodiment, the user holds the lower portion 730 while twisting the upper portion 705. According to another embodiment, the lower portion 730 grips the vial sufficiently to prevent relative rotation, and the user can grasp the vial while twisting the upper portion 705.

As the top portion 705 is twisted, the two or more cantilevers 720 disengage the vial cap from the vial inlet port to expose a portion of the septum (not shown). The window 715 on the vial safety device 700 allows the vial cap to fall out on either side of the vial safety device 700. Although not shown, like the previous embodiments, the vial safety device 400 can include an automatic cap-ejecting mechanism, such as a cantilevered arm that ejects the cap through the window 715 subsequent to the cap being freed from the vial inlet port.

Subsequent to activation, the vial safety device 700 is ready to permit a geometrically compatible syringe (not shown) to access the drug filled vial by way of the female port 710. As previously discussed, when the size and/or shape of the syringe and vial safety device 700 are compatible, the female port 710 guides the syringe proximally toward the vial to ensure proper positioning of a hollow syringe needle (not shown) in relation to the septum (not shown).

Figure 35:
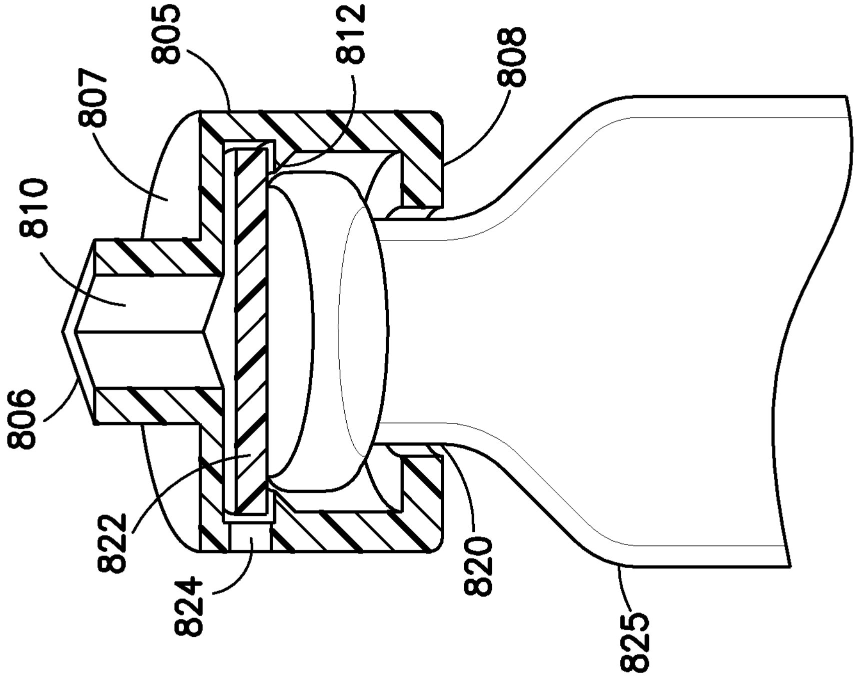
FIGS. 34-36 illustrate a drug vial safety device in accordance with a sixth embodiment of the present invention.
Figure 34:
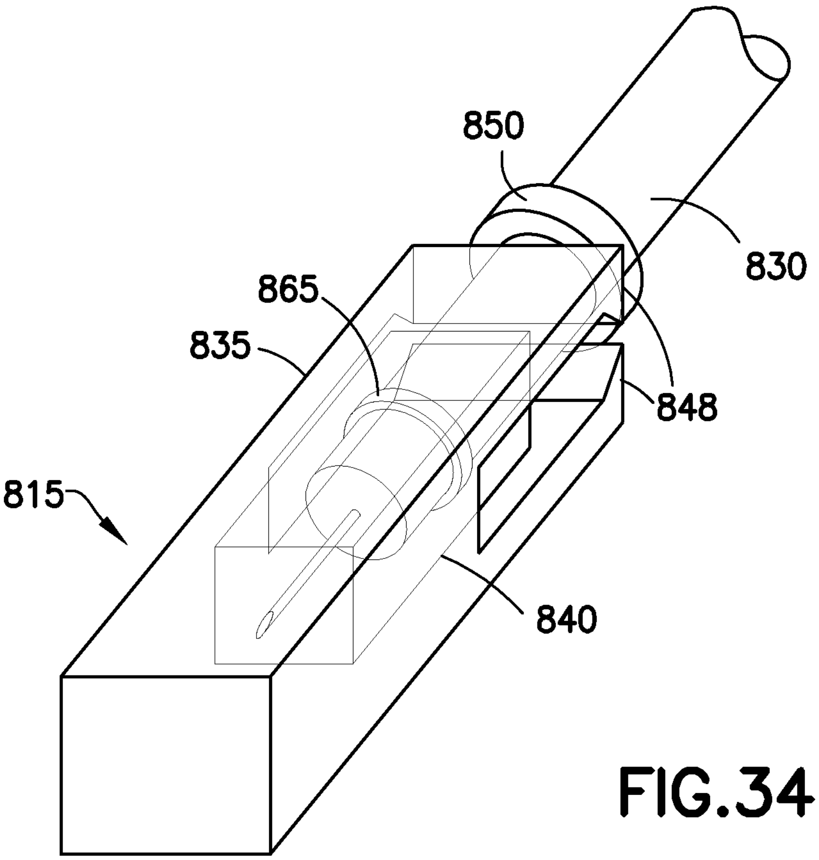
Figure 36:
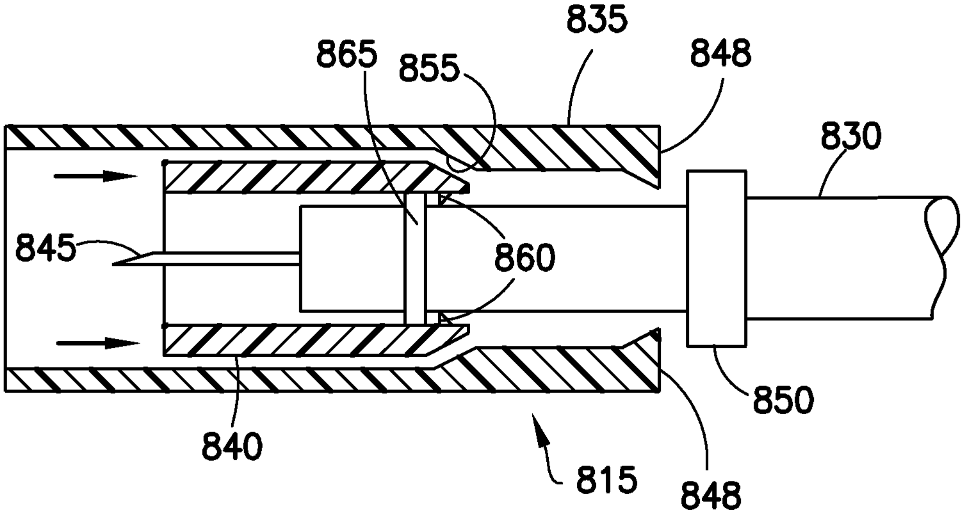

Referring to FIGS. 34-36, a sixth embodiment of a guarded drug vial safety device 800 with a double-shielded syringe is illustrated. This embodiment of a vial safety device 800 includes a vial adapter 805 including a geometrically shaped port 810 and compatible geometrically shaped double-shielded syringe adapter 815. In this embodiment, the port 810 extends away from the vial 825, so that an upper planar surface 806 is substantially parallel to a lower planar surface 807. The vial adapter 805 includes a lip 808 to secure the vial adapter 805 at the neck of the vial, at least one cantilevered arm 812 for removal of the cap 822, and a window 824 for ejecting the cap 822 from the vial adapter 805.

Prior to packaging, the manufacturer fixedly attaches the vial adapter 805 to a neck portion 820 of a vial 825 to shroud a vial inlet port. Additionally, a geometrically compatible double-shielded adapter 815 is fixedly attached to a syringe barrel 830 prior to packaging. The double-shielded syringe adapter 815 includes an outer shield 835 and an inner actuation shield 840. Prior to user activation, the engagement of cantilevered arms 848 with a bottom surface of an outer flange 850 (best shown in FIG. 36) prevents the outer shield 835 from moving farther away from the needle end of the syringe. In addition, as shown in FIG. 36, the interaction between cantilevered arms 860 and an inner flange 865 on the syringe body prevent the inner actuation shield 840 from falling out of the syringe adapter 815.

Also prior to user activation, the syringe barrel 830 is fully guarded by the double-shielded syringe adapter 815. More specifically, the syringe barrel 830 is fully guarded and locked inside the double-shielded syringe adapter 815 until it is mated with the geometrically compatible vial adapter 805.

To activate the device, similar to the vial safety device 100, the user moves the vial adapter 805 distally so that the cantilevered arm 812 displaces the cap 822 from the vial inlet port. The window 824 on the vial adapter 805 allows the vial cap 822 to fall out on either side of the vial adapter 805. Although not shown, like the previous embodiments, the vial safety device 800 can include an automatic cap-ejecting mechanism, such as a cantilevered arm that ejects the cap through the window 824 subsequent to the cap 822 being freed from the vial inlet port.

Next, the user unlocks the double-shielded syringe adapter 815 by pressing the double-shielded syringe adapter 815 down onto the compatible vial adapter 805. The inner perimeter of the outer shield 835 envelops the outer perimeter of the matching vial adapter 805 as the syringe barrel 830 is pressed downward by the user. Simultaneously, as the syringe barrel 830 is forced downward, the inner actuation shield 840 retracts upwardly when a bottom planar surface of the inner actuation shield 840 interacts with the upper planar surface 806 of the vial adapter 805. The movement of the inner actuation shield 840 away from the needle end of the syringe causes the inner actuation shield 840 to engage ramped surfaces 855 of the cantilevered arms 848, thereby displacing the cantilevered arms 848 radially outward. This unlocks the double-shielded syringe adapter 815, allowing the outer flange 850 to bypass the free ends of the cantilevered arms 848, so that an unguarded hollow syringe needle 845 can move toward the vial 825 to penetrate the vial septum at the proper position to withdraw medication from the vial 825.

Although the body of the syringe 830 is depicted as being round and the internal shape of the port 810 is depicted as being, for example, square or diamond-shaped to match its external shape that mates with the outer shield 835, as an additional safety measure, the shape of the body of the syringe 830 can be geometrically compatible with the internal shape of the port 810.

According to one embodiment, the inventive vial safety device can include a magnifying feature to facilitate the reading of scale markings on a syringe.

Another aspect of the present invention can include providing a series of specific syringes to match with specific drugs. In other words, each syringe marking could be customized for a specific drug. For example, a syringe scale could be marked in milligrams or micrograms of a drug rather than in milliliters or cubic centimeters. This would reduce risks as a health care provider would not have the burden of converting measurements prior to drawing a dose from a drug containing vial.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the appended claims and their equivalents.

The invention claimed is:

1. A drug vial safety device, comprising:

a cover securable to drug vial to at least partially enclose at least a neck and a lid of the drug vial;

wherein the cover includes a port having a shape that restricts syringe access to the vial through the port to a syringe shaped to be compatible with the port shape; and wherein the cover comprises:

a cap-separating portion for separating a cap from a drug vial lid; and an ejection window disposed on a lateral side of the cover for removing a separated cap from the cover.

2. The device according to claim 1, wherein the shape of the port restricts access to through the port to a syringe shaped to be complementary with the port shape.

3. The device according to claim 1, wherein the cap-separating portion comprises at least one arm that contacts and lifts the cap from the lid when the cover secured to a drug vial is displaced away from the drug vial.

4. The device according to claim 3, wherein the at least one arm comprises a plurality of arms.

5. The device according to claim 3, wherein the at least one arm comprises at least two arms that are substantially the same length.

6. The device according to claim 3, wherein the at least one arm comprises at least two arms having different respective lengths to provide a shearing force to the cap when the cover secured to the drug vial is displaced away from the drug vial.

7. The device according to claim 3, further comprising a lip that engages the lid to limit displacement of the cover away from the drug vial.

8. The device according to claim 1, wherein the cap-separating portion comprises:

a first portion; and a second portion;

wherein one of the first and second portions comprises a substantially helical cam, and the remaining one of the first and second portions comprises a follower; and wherein rotation of one of the first and second portions relative to the remaining one of the first and second portions drives follower travel on the cam, causing the follower to press radially inward to exert a side force on the cap to separate the cap from lid.

9. The device according to claim 1, further comprising an ejecting mechanism to automatically eject a separated cap from the cover via the ejection window.

10. The device according to claim 9, wherein the ejecting mechanism comprises a cantilevered arm.

11. The device according to claim 10, wherein the cantilevered arms is disposed circumferentially with respect to the cover.

12. The device according to claim 10, wherein the cantilevered arms is disposed axially with respect to the cover.

13. The device according to claim 9, wherein the ejecting mechanism comprises a ramp that is radially displaceable relative to the cover.

14. The device according to claim 13, wherein the ejecting mechanism further comprises a user-actuatable button that upon actuation, radially displaces the ramp relative to the cover.

15. The device according to claim 13, wherein the ejecting mechanism further comprises a user-actuatable button integrally formed with the ramp as a unitary structure.

16. The device according to claim 9, wherein the ejecting mechanism comprises at least one radially inward projection that, upon rotation of at least a portion or the cover, separates the cap from the lid.

17. The device according to claim 1, wherein the cover comprises first and second portions that, together, are connectable to a drug vial to secure the cover to the drug vial.

18. The device according to claim 17, wherein the first portion has at least one tooth and the second portion has at least one corresponding tooth that interlocks with the at least one tooth to secure the cover to the drug vial.

19. The device according to claim 17, wherein the first portion includes a cantilevered arm and the second portion includes a corresponding slot that receives the cantilevered arm to secure the cover to the drug vial.

20. The device according to claim 17, wherein the first and second portions are hingedly connected.

21. The device according to claim 20, wherein the first and second portions are radially securable about the vial's neck.

22. The device according to claim 20, wherein:
the first portion connects to the vial's neck;
the second portion fits over distal end of the first portion; and
the second portion includes at least one hook to secure the second portion to the first portion.

23. The device according to claim 22, wherein the hook includes a clearance to permit displacement of first portion relative to second portion.

24. The device according to claim 22, wherein the first portion comprises a C-shaped ring.

25. The device according to claim 22, wherein the first portion comprises at least one tooth to prevent distal removal of the first portion from a drug vial.

26. The device according to claim 25, wherein the at least one tooth comprises a plurality of cantilevered arms.

27. The device according to claim 26, wherein the cantilevered arms are angled relative to a radial direction of the cover.

28. The device according to claim 27, wherein the cover comprises an ejecting mechanism to automatically eject a separated cap from the cover via the ejection window.

29. The device according to claim 17, wherein:
the first portion includes a lip; and
the second portion has at least one tooth that engages the lip to prevent distal removal of the second portion from the first portion.

30. The device according to claim 17, wherein:
the first portion has a thread, and
the second portion has a complimentary thread, permitting rotational movement of second portion relative to first portion to generate distal displacement of second relative to first.

31. The device according to claim 30, one of the first and second portions comprises at least one structure that contacts and lifts the cap from lid when the cover secured to a drug vial is displaced away from the drug vial.

32. The device according to claim 31, wherein the at least one structure comprises a lip.

33. The device according to claim 31, wherein the at least one structure comprises a plurality of cantilevered arms.

34. The device according to claim 31, wherein the cover comprises an ejecting mechanism to automatically eject a separated cap from the cover via the ejection window.

35. A combination, comprising:
the safety device of claim 1; and
a drug vial.

36. The combination according to claim 35, further comprising a syringe having a shape compatible with the port of the safety device.

37. The combination according to claim 36, wherein:
the port of the cover extends away from the drug vial; and
the syringe has an outer shield with a shape that is compatible with the port.

38. The combination according to claim 37, wherein:
the syringe includes an inner activation shield that is moveable relative to the outer shield; and
movement of the inner activation shield away from the vial unlocks the outer shield relative to the syringe, thereby permitting a hollow syringe needle to move toward and access medicament in the vial.

39. A method of readying a vial for removal of medicament therein and ensuring proper correlation between medicament in the drug vial and a syringe, the method comprising:
providing a syringe with a shaped portion and a hollow needle;
securing a cover to the drug vial to at least partially enclose at least a neck and a lid of the drug vial;
wherein the cover includes a port having a shape that is compatible with the shaped syringe portion;
wherein the port permits passage of at least part of the shaped syringe portion therethrough to provide the needle with access to the medicament within the drug vial;
subsequent to securing the cover to the drug vial, moving the cover relative to the drug vial to separate a cap from a lid of the drug vial with a cap-separating portion of the cover; and
ejecting the separated cap through an ejection window disposed on a lateral side of the cover.

* * * * *